United States Patent [19]

Kaieda et al.

[11] Patent Number: 4,689,179
[45] Date of Patent: Aug. 25, 1987

[54] METHOD FOR PRODUCTION OF FLUORINATED QUINONES

[75] Inventors: Osamu Kaieda, Osaka; Koichi Hirota, Suita; Hideki Itoh, Kyoto; Masaru Awashima, Suita; Toshiaki Nakamura, Osaka, all of Japan

[73] Assignee: Nippon Shokubai Kagaku Kogyo Co., Ltd., Japan

[21] Appl. No.: 756,028

[22] Filed: Jul. 17, 1985

[30] Foreign Application Priority Data

Jul. 30, 1984 [JP] Japan ................................. 59/157527
Jul. 30, 1984 [JP] Japan ................................. 59/157529

[51] Int. Cl.$^4$ .................... C07C 50/18; C07C 50/12; C07D 307/89
[52] U.S. Cl. ............................... 260/384; 260/396 R; 260/694; 549/247
[58] Field of Search .................. 260/384, 396 R, 694; 549/247

[56] References Cited

U.S. PATENT DOCUMENTS 2,013,030  9/1935  Calcott et al. ................... 260/384
2,347,846  5/1944  Scherer .
2,891,074  6/1959  Scherer et al. ................... 260/384

FOREIGN PATENT DOCUMENTS 164615  9/1964  U.S.S.R. ............................... 260/384

OTHER PUBLICATIONS

Weast et al, CRC Handbook of Chemistry and Physics' 63rd ed., 1983, pp. C-159.
Christie, et al., Chem. Ber., (1963), 96 2537.
Jo. of Org. Synthetic Chem. Soc., Ishikawa, 25, 808, (1967).
Chemistry of Org. Fluorine Cpds., Hudlicky, 112, (1976).
Tr.Zhur.Ohscheh.Khim., Yakobson, et al., 36, 142, (1966).
Chem. Ber., Wallenfels, et al., 90, 2819, (1957).
Condensed Aromatic Cpds., 64, 17509, (1966).

Primary Examiner—Glennon H. Hollrah
Assistant Examiner—Raymond Covington

[57] ABSTRACT

A method for the production of a fluorinated quinone, which comprises causing a chlorinated aromatic compound represented by the general formula I:

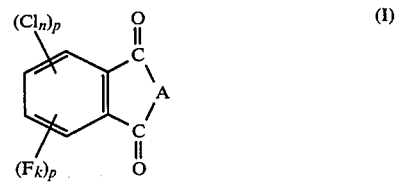

wherein A denotes O,

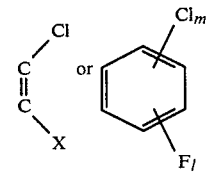

(where m denotes an integer of the value of 1 to 4 and l denotes an integer of the value of 0 to 3), X denotes Cl, F, or H, n denotes an integer of the value of 0 to 4, k denotes an integer of the value of 0 to 3, and p denotes 0 to 1, providing that p is 1 and n is not zero where A is O, to react in benzonitrile as a medium at a temperature in the range of 190° to 400° C. with at least one fluorinating agent selected from the group consisting of alkali metal fluorides and alkaline earth metal fluorides under spontaneously generating pressure.

11 Claims, No Drawings

METHOD FOR PRODUCTION OF FLUORINATED QUINONES

BACKGROUND OF THE INVENTION

1. Field of the Invention:

This invention relates to a method for the production of fluorinated quinones. More particularly, this invention relates to a method for the production of fluorinated quinones by the halogen exchange reaction of chlorinated aromatic compounds with a fluorinating agent.

2. Description of the Prior Art:

The so-called halogen exchange reaction, namely the exchange of fluorine and other halogen atoms by the reaction of an alkali fluoride upon aromatic halides has long been known to the art. Generally, such halogen exchange reactions are carried out mainly in such aprotic polar solvents as dimethyl sulfoxide (DMSO), sulfolane (TMSO $_2$), N-dimethylformamide (DMF), N-methyl-2-pyrrolidone (NMP), and dimethyl sulfone (DMSO $_2$) at temperatures below the boiling points of these solvents [e.g. Ishikawa: Journal of organic Synthetic Chemical Society, Japan, Vol. 25, Page 808 (1967), and M. Hudlicky, Chemistry of Organic Fluorine Compounds, page 112 (1976), John Wiley & Sons Press]. Some cases have been reported in which phase transfer catalysts such as crown compounds were added for the purpose of expediting reactions involved.

The solvents generally used in halogen exchange reactions are such that when reaction temperatures are elevated for improving yields or when the solvents themselves are used for a long time, the solvents undergo decomposition or react with raw materials or reaction products to give rise to by-products and eventually impair yields. Further, these solvents have the disadvantage that they are not so easily recovered or reclaimed as to render their commercial use feasible. To avoid the drawback that these solvents are not effectively used at elevated temperatures, the practice of carrying out the halogen exchange reactions at elevated temperatures ranging from 190° to 500° C. in an autoclave without use of a solvent has found popular acceptance.

Separately methods for synthesizing fluorinated quinones from chlorinated quinones have been known to the art. A case is published in G. G. Yakobson et al.: Tr. Zhur. Ohschch. Khim., Vol. 36, page 142 (1966) in which 2,3-difluoro-1,4-naphthoquinone was synthesized by the halogen exchange reaction from 2,3-dichloro-1,4-naphthoquinone at 190° to 195° C. in an autoclave without use of a solvent.

In K. Wallenfels et al.: Chem. Ber., Vol. 90, page 2819 (1957), a case is published in which 1,2,3,4-tetrafluoroanthraquinone was synthesized by the halogen exchange reaction from 1,2,3,4-tetrachloroanthraquinone at 220° to 250° C. in an autoclave without use of a solvent.

It is safely inferred that since these methods invariably avoid using a solvent, the reactions generate heat and, therefore, the reaction systems offer the problem of difficult temperature control, and a large amount of carbonized materials remains fast to the vessel, rendering the methods themselves hardly feasible from the commercial point of view.

Methods for synthesizing octafluoroanthraquinone from tetrachlorophthalic anhydride have also been known to the art. One of such methods is disclosed in G. G. Yakobson et al.: Tetrahedron Letters, page 4473 (1965), for example. This method consists in heating tetrachlorophthalic anhydride at a temperature of 300° C. in an autoclave in the absence of a solvent thereby subjecting the anhydride to both decarboxylation and halogen exchange and giving birth to octafluoroanthraquinone.

This method does not give the product in a satisfactorily high yield. Further, since this method uses no solvent, the reaction generates heat and, therefore, the reaction system offers the problem of difficult temperature control, and the reaction vessel suffers from heavy deposition of carbonized materials, rendering the method itself infeasible from the commercial point of view.

An object of this invention, therefore, is to provide a novel method for the production of fluorinated Another object of this invention is to provide a method for the production of fluorinated quinones in a high yield by the halogen exchange reaction of chlorinated aromatic compounds with a fluorinating agent.

SUMMARY OF THE INVENTION

The objects described above are attained by a method for the production of a fluorinated quinone, which comprises causing a chlorinated aromatic compound represented by the general formula I:

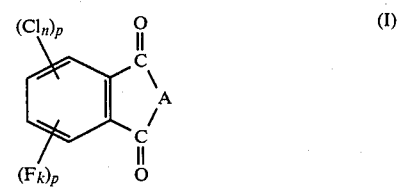

wherein A denotes O,

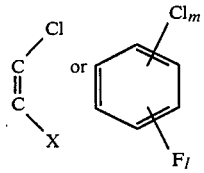

(where m denotes an integer of the value of 1 to 4 and denotes an integer of the value of 0 to 3), X denotes Cl, F, or H, n denotes an integer of the value of 0 to 4, k denotes an integer of the value of 0 to 3, and p denotes 0 or 1, providing that p is 1 and n is not zero where A is O, to react in benzonitrile as a medium at a temperature in the range of 190° to 400° C. with at least one fluorinating agent selected from the group consisting of alkali metal fluorides and alkaline earth metal fluorides under spontaneously generating pressure.

EXPLANATION OF PREFERRED EMBODIMENT

The chlorinated aromatic compound to be used as the starting material in this invention is a compound represented by General Formula I. Typical examples of the chlorinated aromatic compound are chlorinated phthalic anhydrides such as tetrachlorophthalic anhydride and 3,6-dichloro-4,5-difluorophthalic anhydride, and chlorinated quinones such as 2,3-dichloro-1,4-naphthoquinone, 2-chloro-3-fluoro-1,4-naphthoquinone, 2- chloro-1,4-naphthoquinone, 1,2,3,4-tetrachloroanthraquinone, 1,4-dichloro-2,3-difluoroanthraquinone, 2,3-dichloroanthraquinone, and octachloroanthraquinone. Among other chlorinated aromatic compound cited above, tetrachlorophthalic anhydride, 2,3-dichloro-1,4-naphthoquinone, and 1,2,3,4-tetrachloroanthraquinone are particularly desirable. By the reaction, octafluoroanthraquinone and the like are produced from chlorinated phthalic anhydrides, 2,3-difluoro-1,4-naphthoquinone, 2-chloro-3-fluoro-1,4-naphthoquinone, 2-fluoro-1,4-naphthoquinone and the like from chlorinated naphthoquinones, and 1,2,3,4-tetrafluoroanthraquinone, 1,4-dichloro-2,3-difluoroanthraquinone, 2,3-difluoroanthraquinone, octafluoroanthraquinone and the like from chlorinated anthraquinones respectively.

Since the solvent benzonitrile in the present invention is thermally stable, it can be effectively used even at temperatures in the range of 190° to 400° C., the temperature range considered necessary for the production of octafluoroanthraquinone, tetrafluoroanthraquinone, difluoronaphthoquinone, etc. from tetrachlorophthalic anhydride, chlorinated quinones, etc. by the halogen exchange reaction. It also has the advantage that this solvent does not entail the secondary reaction which is observed between certain solvents and reactants or resultant reaction products. Moreover, because of the use of this solvent, the method of this invention, unlike the aforementioned method using no solvent, permits easy temperature control and avoids heavy formation of a carbonated materials and enjoys the advantage of obtaining the product in a high yield.

Unlike aprotic polar solvents which are used generally, the benzonitrile used as the solvent in this invention has only a minimal ability to dissolve inorganic salts at temperatures below its boiling point. In the ordinary halogen exchange reaction now in common use, there must be used a solvent capable of dissolving a fluoride being used as a fluorinating agent. Thus, the conventional halogen exchange reaction uses as aprotic polar solvent such as, for example, DMSO, TMSO$_2$, DMF, NMP or DMSO$_2$ which is highly capable of dissolving inorganic salts. Use of benzonitrile, a solvent which is minimally capable of dissolving inorganic salts, as contemplated in this invention has been set aside as disadvantageous for the conventional halogen exchange.

By our study, it has been ascertained that when benzonitrile is used at temperatures exceeding the boiling point thereof, the solubility of the fluorinating agent such as potassium fluoride is sharply increased and that in the case of the present invention, the reaction proceeds advantageouly when it is performed at temperatures in the range of 190° to 400° C. The strikingly high yield in which this invention affords the fluorinated quinones may be safely ascribed to the fact that the use of benzonitrile as the solvent brings about advantageous temperature effects and, at the same time, increases the ability of the fluorinating agent.

Generally, as the fluorinating agent for the halogen exchange reaction, alkali fluorides such as cesium fluoride, potassium fluoride, and sodium fluoride and alkaline earth metal fluorides such as barium fluoride and calcium fluoride are used frequently. At times, fluorides of transition metals such as antimony fluoride are also available. For the purpose of this invention, any of the generally accepted fluorinating agents can be used. In all the fluorinating agents usable at all, potassium fluoride which is readily available commercially proves particularly desirable.

The fluorinating agent is required to be used at least in an equivalent amount relative to the chlorine atom in the chlorinated aromatic compound to be substituted by a fluorine atom. Potassium fluoride, for examples, is required to be present in at least 4 mols per mol of tetrachlorophthalic anhydride. Preferably, the amount of potassium fluoride falls in the range of 4 to 8 mols per mol of tetrachlorophthalic anhydride.

Where potassium fluoride is used as the fluorinating agent and 2,3-dichloro-1,4-naphthoquinone as the starting material, the fluorinating agent has only to be present in at least two mols per mol of the raw material. Preferably, the amount of potassim fluoride is desired to fall in the range of 2 to 4 mols per mol of 2,3-dichloro-1,4-naphthoquinone. Where potassium fluoride is used as the fluorinating agent and 1,2,3,4-tetrachloroanthraquinone as the starting material, the fluorinating agent is only required to be in at least 4 mols per mol of the raw material. Preferably, the amount of potassium fluoride is desired to fall in the range of 4 to 8 mols per mol of 1,2,3,4-tetrachloroanthraquinone.

The reaction temperature is in the range of 190° to 400° C. Where a chlorinated phthalic anhydride is used as the starting material, the reaction temperature falls more desirably in the range of 270° to 400° C. and most desirably in the range of 300° to 350° C. Where a halogenated quinone is used as the starting material, the reaction temperature falls more desirably in the range of 190° to 340° C. and most desirably in the range of 200° to 280° C.

If the reaction is carried out at a lower temperature, it is liable to produce a compound in which part of the fluorine component of the raw material remains in an unaltered form. If the reaction is carried out at a higher temperature, it gives birth to a carbonized materials which persists in the produced compound. In either case, the yield of fluorinated quinone is insufficient.

Since this invention requires the reaction to proceed under spontaneously generated pressure, the pressure during the initial stage of the reaction falls in the range of about 1.5 to about 16 kg/cm$^2$ (gauge) at temperatures in the range of 200° to 350° C. Particularly when a chlorinated phthalic anhydride is used as the raw material, the pressure of the reaction system is in the range of about 6 to about 16 kg/cm$^2$ (gauge) at temperatures in the range of 300° to 350° C. As the reaction proceeds, it gradually liberates carbon dioxide and the pressure further increases. When a chlorinated quinone is used as the starting material, the pressure falls in the range of about 1.5 to about 8 kg/cm$^2$ (gauge) at temperatures in the range of 200° to 280° C. Optionally, this pressure may be increased by introduction of an inert gas such as nitrogen when necessary.

Properly, the reaction time falls in the range of about 2 to 48 hours, preferably 5 to 30 hours, although it is variable with the reaction temperatures used.

The chlorinated aromatic compound as the starting material is desired to be added to the reaction system in an amount in the range of about 5 to 50 parts by weight, preferably 15 to 35 parts by weight, per 100 parts by weight of the solvent. After completion of the reaction, the reaction solution is cooled to room temperature and the suspended inorganic salts such as potassium chloride and the unaltered fluorinating agent such as potassium fluoride are removed by any of the conventional methods of solid-liquid separation such as, for example, filtration. Thereafter, the benzonitrile solution containing the fluorinated quinone is evaporated to expel the solvent benzonitrile and recover the crude fluorinated quinone in the form of residue. Since fluorinated quinone is a sublimable substance, part of the produced fluorinated quinone is distilled out in conjunction with the solvent. By using the recovered benzonitrile as the solvent in the next round of halogen exchange reaction, the part of fluorinated quinone entrained by the solvent can be effectively reclaimed.

The crude fluorinated quinone obtained as described above can be refined by sublimation, distillation, etc.

It is generally held that the halogen exchange reaction proceeds more advantageously in the absence of water so long as circumstances permit, because the absence of water serves to heighten the reaction velocity and preclude the occurrence of secondary reaction. Such aprotic polar solvents as DMSO, TMSO$_2$, DMF, NMP, and DOSO$_2$ which are in popular use are highly hygroscopic and contain water in fairly large amounts. Prior to use in the reaction, therefore, the solvent must be deprived of the entrained water through azeotropic distillation with benzene or toluene. The present invention, in principle, has no use for this pretreatment because benzonitrile is not a hygroscopic compound. In contrast, potassium fluoride or other similar fluoride which is used as the fluorinating agent possesses a high degree of hygroscopicity and, at times, is desired to be deprived of the entrained water through azeotropic distillation with benzene or toluene. For this invention, the presence of an phase transfer catalyst in the reaction system is optional. The presence of this phase transfer catalyst has the advantage of increasing the reaction velocity and decreasing the reaction time.

As the phase transfer agent, a crown compound such as dibenzo-18-crown-6-ether or polyethylene glycol having a molecular weight in the range of 300 to 600 can be used.

The amount of this catalyst is properly in the range of 0.01 to 0.25 mol per mol of the chlorinated aromatic compound.

Now, the present invention will be described more specifically below with reference to working examples. It should be noted, however, that this invention is not limited to these working examples.

EXAMPLE 1

An autoclave of stainless steel having an inner volume of 500 ml was charged with 200 g of benzonitrile, 60.0 g (0.21 mol) of tetrachlorophthalic anhydride, and 73.2 g (1.26 mols) of dry potassium fluoride in the form of finely divided particles. With the air in the autoclave displaced with nitrogen gas, the contents of the autoclave were heated and stirred for reaction at 320° C. for 18 hours (in initial stage 11.0 kg/cm$^2$·G). After completion of the reaction, the reaction mixture was cooled to room temperature and the suspended potassium chloride and the unaltered potassium fluoride were removed by filtration. When the benzonitrile solution as mother liquor was analyzed by the internal standard method of gas chromatography using 2 m of SE 52 as a packing material at 150° C., it was found that the reaction produced 80.3 mol% of octafluoroanthraquinone, 6.3 mol% of dichlorodifluorophthalic anhydride, and 5.8 mol% of pentafluorobenzoyl fluoride based on the tetrachlorophthalic anhydride used as the starting material. With a rotary evaporator, the mother liquor was distilled to expel benzonitrile under the final conditions of 120° C. and 30 Torrs. The residue of the distillation, on sublimation, gave 26.2 g of octafluoroanthraquinone. When this fraction was analyzed by gas chromatography, peaks of other components than octafluoroanthraquinone were substantially undiscernible.

EXAMPLE 2

An autoclave of stainless steel having an inner volume of 200 ml was charged with 100 g of benzonitrile, 32 g (0.141 mol) of 2,3-dichloro-1,4-naphthoquinone, and 19.7 g (0.338 mol) of dry potassium fluoride in the form of finely divided particles. With the air in the autoclave displaced with nitrogen gas, the contents of the autoclave were heated and stirred for reaction at 210° C. (3.0 kg/cm$^2$·G) for 16 hours. After completion of the reaction, the reaction mixture was cooled to room temperature and the suspended potassium chloride and the unaltered potassium fluoride were removed by filtration. The benzonitrile solution as the mother liquor was analyzed by the internal standard method of gas chromatography at 110° C. with 2 m of SE 52 as the packing agent. It was found consequently that the reaction produced 87.3 mol% of 2,3-difluoro-1,4-naphthoquinone and 1.2 mol% of 2-chloro-3-fluoro-1,4-naphthoquinone based on the 2,3-dichloro-1,4-naphthoquinone used as the starting material. With a rotary evaporator, the mother liquor was distilled to expel benzonitrile under the final conditions of 120° C. and 30 Torrs. The residue of the distillation, on sublimation, gave 20.6 g of 2,3-difluoro-1,4-naphthoquinone. When this fraction was analyzed by gas chromatography, peaks of other components than 2,3-difluoro-1,4-naphthoquinone were substantially undiscernible.

EXAMPLE 3

An autoclave of stainless steel having an inner volume of 200 ml was charged with 100 g of benzonitrile, 30 g (0.087 mol) of 1,2,3,4-tetrachloroanthraquinone, and 24.3 g (0.418 mol) of dry potassium fluoride in the form of finely divided particles. With the air in the autoclave displaced with nitrogen gas, the contents of the autoclave were heated and stirred for reaction at 270° C. for 24 hours. The reaction mixture was treated and analyzed by following the procedure of Example 2. Consequently, the reaction produced 90.6 mol% of 1,2,3,4-tetrafluoroanthraquinone.

EXAMPLE 4

An autoclave was charged with the same raw materials as used in Example 1, except that the reaction was carried out at a temperature of 350° C. for 14 hours. After the reaction was terminated, the reaction mixture was treated by following the procedure of Example 1. When the mother liquid consequently obtained was analyzed by gas chromatography, it was found to obtain 84.5 mol% of octafluoroanthraquinone, 1.4 mol% of dichlorodifluorophthalic anhydride and 7.8 mol% of pentafluorobenzoyl fluoride based on the amount of tetrachlorophthalic anhydride first places in the autoclave.

EXAMPLE 5

An autoclave was charged with the same raw materials as in Example 2, except that the reaction was carried out at a temperature of 190° C. for 8 hours. After the reaction was terminated, the reaction mixture was treated by following the procedure of Example 1. When the mother liquid consequently obtained was analyzed by gas chromatography, it was found to obtain 82.7 mol% of 2,3-difluoro-1,4-naphthoquinone and 8.2 mol% of 2-chloro-3-fluoro-1,4-naphthoquinone based on the 2,3-dichloro-1,4-naphthoquinone first places in the autoclave.

EXAMPLE 6

An autoclave having an inner volume of 500 cc was charged with the same raw materials as used in Example 1, except that 5.75 g (0.016 mol) of dibenzo-18-crown-6-ether was dissolved in benzonitrile. The contents of the autoclave were stirred at 300° C. for 20 hours. After the reaction was terminated, the reaction mixture was treated by following the procedure of Example 1. When the mother liquid consequently obtained was analyzed by gas chromatography, it was found to contain 77.7 mol% of octafluoroanthraquinone, 14.8 mol% of dichlorodifluorophthalic anhydride and 2.3 mol% of pentafluorobenzoyl fluoride based on the amount of tetrachlorophthalic anhydride first placed in the autoclave.

What is claimed is:

1. A method for the production of a fluorinated quinone, which comprises causing a chlorinated aromatic compound represented by the general formula I:

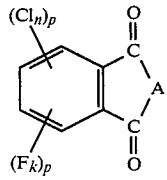

wherein A denotes O,

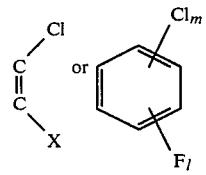

(where m denotes an integer of the value of 1 to 4 and l denotes an integer of the value of 0 to 3), X denotes Cl, F, or H, n denotes an integer of the value of 0 to 4, k denotes an integer of the value of 0 to 3, and p denotes 0 or 1, providing that p is 1 and n is not zero where A is O, to react in benzonitrile as a medium at a temperature in the range of 190° to 400° C. with at least one fluorinating agent selected from the group consisting of alkali metal fluorides and alkaline earth metal fluorides under spontaneously generating pressure.

2. A method according to claim 1, wherein the amount of said fluorinating agent is at least an equivalent amount relative to the chlorine atom in said chlorinated aromatic compound to be substituted by fluorine atom.

3. A method according to claim 2, wherein said chlorinated aromatic compound is tetrachlorophthalic anhydride and said fluorinated quinone is octafluoroanthraquinone.

4. A method according to claim 3, wherein said reaction is carried out at a temperature in the range of 270° to 400° C.

5. A method according to claim 2, wherein said chlorinated aromatic compound is a chlorinated quinone.

6. A method according to claim 5, wherein said reaction is carried out at a temperature in the range of 190° to 340° C.

7. A method accoridng to claim 5, wherein said chlorinated quinone is 2,3-dichloro-1,4-naphthoquinone, said fluorinated quinone is 2,3-difluoro-1,4-naphthoquinone, and said reaction is carried out at a temperature in the range of 190° to 280° C.

8. A method according to claim 5, wherein said chlorinated quinone is 1,2,3,4-tetrachloroanthraquinone, said fluorinated quinone 1,2,3,4-tetrafluoroanthraquinone, and said reaction is carried out at a temperature in the range 200° to 340° C.

9. A method according to claim 2, wherein said fluorinating agent is potassium fluoride.

10. A method according to claim 2, wherein said reaction is carried out in the presence of a phase transfer catalyst.

11. A method according to claim 2, wherein the amount of said phase transfer agent to be used is in the range of 0.01 to 0.25 mol per mol of said chlorinated aromatic compound.

* * * * *